(12) United States Patent
Van Heerden

(10) Patent No.: US 7,175,634 B2
(45) Date of Patent: Feb. 13, 2007

(54) UTERINE MANIPULATOR DEVICE

(76) Inventor: Marcus Vincent Van Heerden, 47 Destades Road, Colleen Glen, 6018, Port Elizabeth (ZA)

( * ) Notice: Subject to any disclaimer, the term of this patent is extended or adjusted under 35 U.S.C. 154(b) by 569 days.

(21) Appl. No.: 10/469,055

(22) PCT Filed: Feb. 20, 2002

(86) PCT No.: PCT/IB02/00504

§ 371 (c)(1),
(2), (4) Date: Jan. 14, 2004

(87) PCT Pub. No.: WO02/065924

PCT Pub. Date: Aug. 29, 2002

(65) Prior Publication Data

US 2004/0111097 A1 Jun. 10, 2004

(30) Foreign Application Priority Data

Feb. 20, 2001 (ZA) .................................. 2001/1415

(51) Int. Cl.
*A61B 17/42* (2006.01)
(52) U.S. Cl. .................................................. 606/119
(58) Field of Classification Search ........ 606/119–124, 606/193, 194, 197; 604/279, 254
See application file for complete search history.

(56) References Cited

U.S. PATENT DOCUMENTS

| | | | |
|---|---|---|---|
| 4,559,944 A | 12/1985 | Jaeger | |
| 5,643,285 A * | 7/1997 | Rowden et al. | 606/119 |
| 5,697,937 A * | 12/1997 | Toma | 606/119 |
| 5,840,077 A * | 11/1998 | Rowden et al. | 606/193 |
| 5,980,534 A | 11/1999 | Gimpelson | |
| 6,156,006 A * | 12/2000 | Brosens et al. | 604/104 |
| 6,293,952 B1 * | 9/2001 | Brosens et al. | 606/119 |

FOREIGN PATENT DOCUMENTS

DE 10 84 427 B 6/1960

* cited by examiner

Primary Examiner—Anhtuan T. Nguyen
(74) Attorney, Agent, or Firm—Wells St. John P.S.

(57) ABSTRACT

A uterine manipulator device for injecting a visualisation fluid into the uterine cavity of a female via the cervix. The device comprises an elongate body, a tanaculum for gripping the cervix and an inflatable bladder for forming a fluid-resistant seal with the cervix. The elongate body has a conduit along which visualisation fluid can be conveyed to the uterus and a conduit for air, having an outlet opening, which is connectable to a pressurized air supply. The bladder is mounted on the elongate body over the outlet opening, surrounding the elongate body and sealed to the elongate body at opposite ends of the bladder. The bladder includes an outer sealing element which, upon inflation, forms a fluid-tight seal with the cervix, and an inner sleeve which fits over the opening preventing a return flow of air, yet allowing pressurized air into the bladder for inflating it.

8 Claims, 3 Drawing Sheets

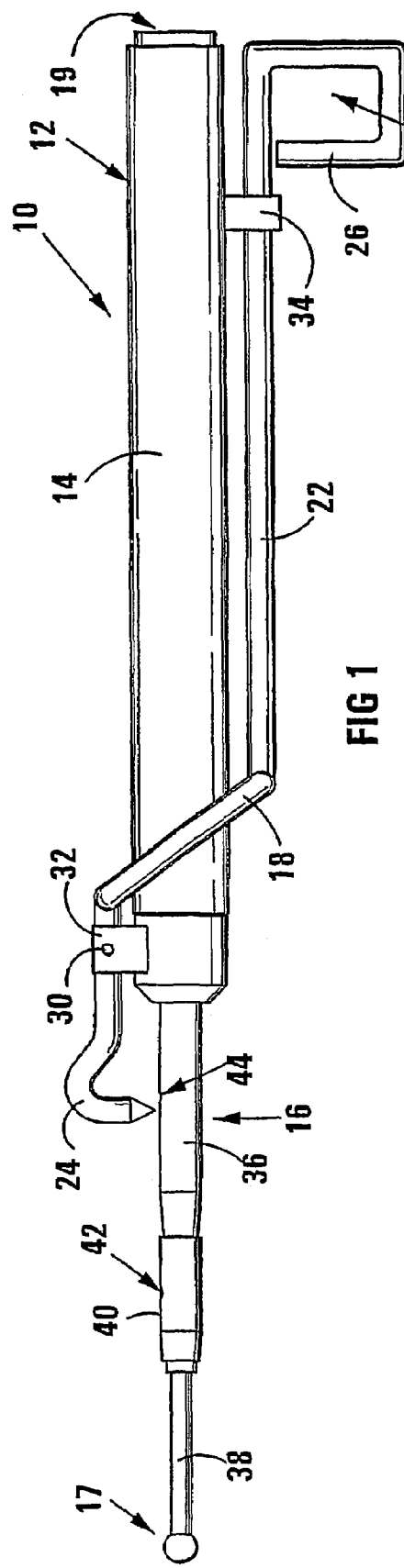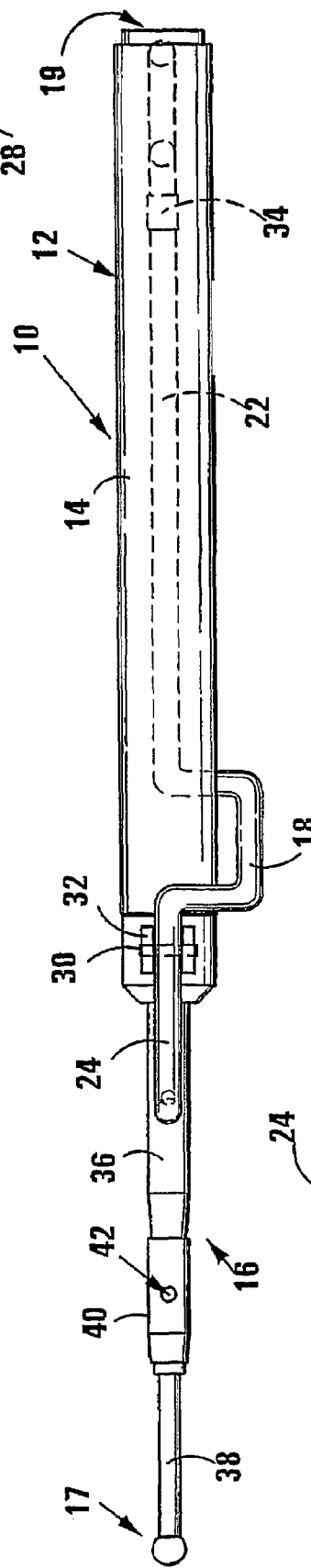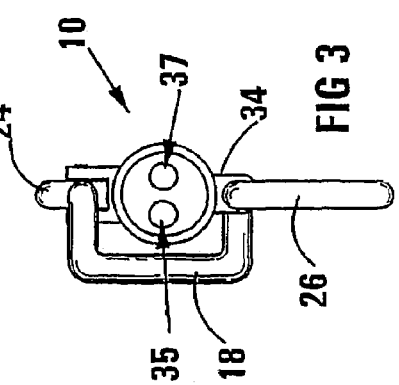

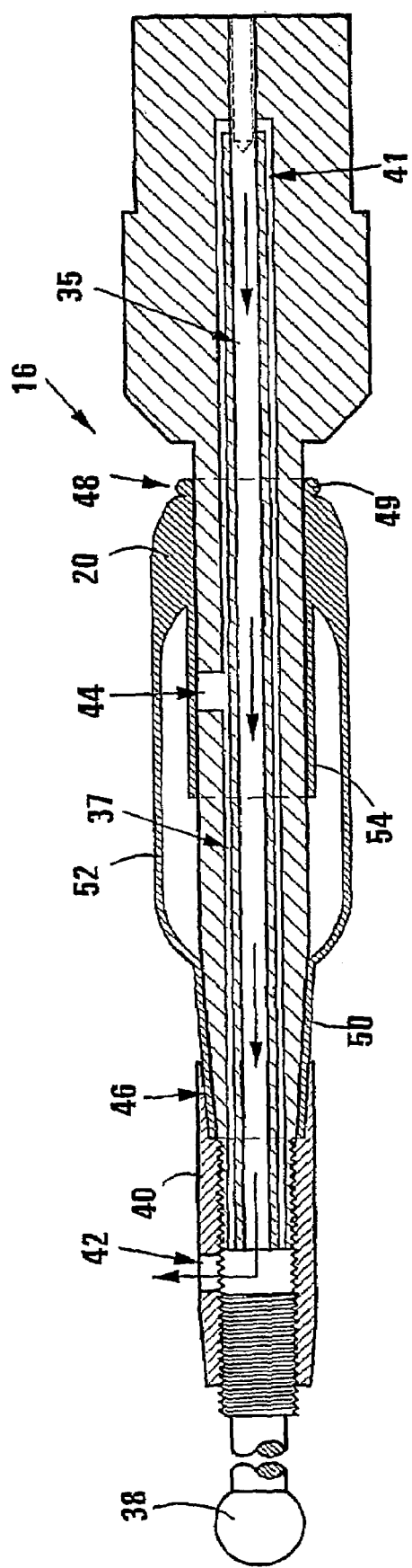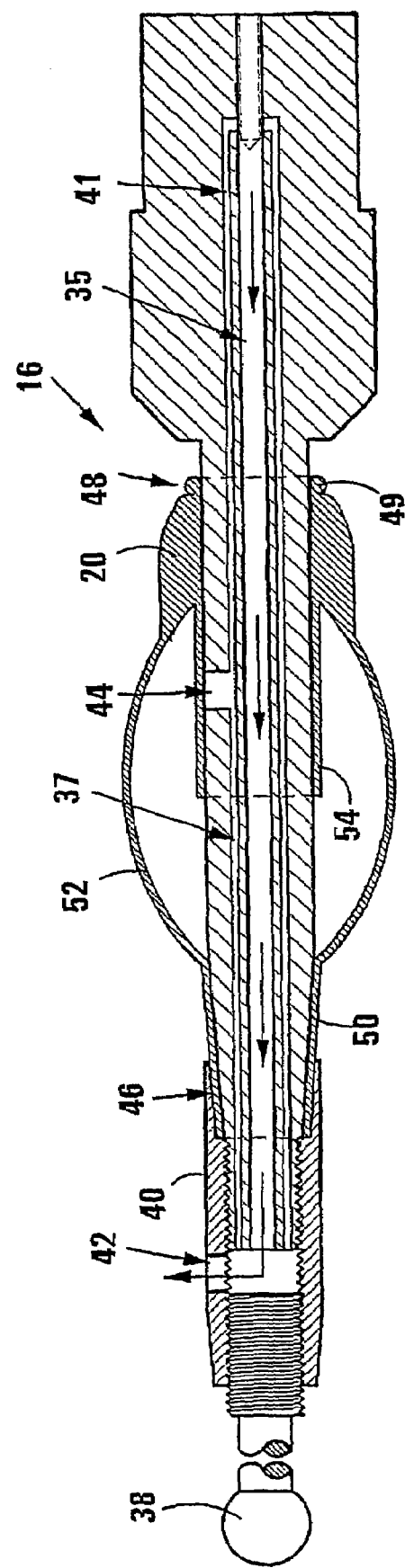

UTERINE MANIPULATOR DEVICE

CROSS REFERENCE TO RELATED APPLICATION

This application claims priority under 35 U.S.C. § 371 to PCT International Application Number PCT/IB02/00504 filed Feb. 20, 2002, which claims priority to RSA Patent Application 2001/1415 filed Feb. 20, 2001.

FIELD OF INVENTION

THIS INVENTION relates to a uterine manipulator device.

It relates particularly to a uterine manipulator device for injecting a visualisation fluid into the uterus of a female via the cervix. It also relates to a sealing device for use with the uterine manipulator device.

According to a first aspect of the invention there is provided a uterine manipulator device for injecting a visualisation fluid into the uterus of a female via the cervix, the uterine manipulator device comprising an elongate body that can be inserted into the uterus of the female via the cervix, the elongate body having a visualisation fluid conduit along which the visualisation fluid can be conveyed to the uterus and a gas conduit along which a gas can be conveyed, the gas conduit defining an outlet opening for the gas;

gripping means that is connected to the elongate body, for releasably gripping the cervix; and sealing means that is locatable, in use, in the cervical canal of the female and that is in the form of an inflatable bladder of resiliently deformable material having two ends and defining an opening at each end, the bladder being mounted to the elongate body in an arrangement wherein the bladder surrounds a part of the elongate body, with the elongate body extending through the openings of the bladder and the ends thereof being secured to the elongate body to form a fluid-tight seal therewith, the bladder comprising an outer inflatable sealing element and an inner valve element in the form of a sleeve which extends inwardly from one of the ends of the bladder, terminating short of the other end thereof, the sleeve fitting over the outlet opening of the gas conduit so as to form a gas-tight seal preventing a return-flow of gas into the gas conduit from the bladder, the sleeve being resiliently deformable under the force of a pressurised gas flowing in the gas conduit, in use, so as to allow the flow of gas into the bladder for inflating it to form a fluid-resistant seal between the elongate body and the wall of the cervical canal, in use, thereby preventing a return-flow of visualisation fluid.

The outer inflatable sealing element may be substantially elongate and tubular in the inflated state.

The outer inflatable sealing element may have a configuration permitting it to conform substantially to the wall of the cervical canal in the inflated state.

The elongate body may comprise a main body portion and a nose portion that can be inserted into the cervix, the elongate body defining said gas conduit, with the outlet opening thereof being disposed in a region of the nose portion surrounded by the bladder.

The gripping means may be in the form of a tanaculum.

According to a second aspect of the invention there is provided a sealing device for use with a uterine manipulator device for injecting a visualisation fluid into the uterus of a female via the cervix, wherein wherein the uterine manipulator device includes an elongate body that can be inserted into the uterus of the female via the cervix, the elongate body having a visualisation fluid conduit along which the visualisation fluid can be conveyed to the uterus and a gas conduit along which a gas can be conveyed, the gas conduit defining an outlet opening for the gas, the sealing device being locatable, in use, in the cervical canal of the female and being mountable on the elongate body so as to form a fluid-resistant seal between the elongate body and the wall of the cervical canal thereby to prevent a return flow of visualisation fluid, the sealing device comprising an inflatable bladder of resiliently deformable material having two ends and defining an opening at each end, the bladder being mountable to the elongate body in an arrangement wherein the bladder surrounds a part of the elongate body having said outlet opening for the gas conduit, with the elongate body extending through the openings of the bladder and the ends thereof being secured to the elongate body to form a fluid-tight seal therewith, the bladder comprising an outer inflatable sealing element and an inner valve element in the form of a sleeve which extends inwardly from one of the ends of the bladder, terminating short of the other end thereof, the sleeve fitting over the outlet opening of the gas conduit so as to form a gas-tight seal preventing a return-flow of gas into the gas conduit from the bladder, the sleeve being resiliently deformable under the force of a pressurised gas flowing in the gas conduit, in use, so as to allow the flow of gas into the bladder for inflating it to form said fluid-resistant seal between the elongate body and the wall of the cervical canal, in use.

The outer inflatable sealing element may be substantially elongate and tubular in the inflated state.

The outer inflatable sealing element may have a configuration permitting it to conform substantially to the wall of the cervical canal in the inflated state.

BRIEF DESCRIPTION OF THE DRAWINGS

Further features of the invention are described hereinafter by way of a non-limiting example of the invention, with reference to and as illustrated in the accompanying diagrammatic drawings. In the drawings:

FIG. 1 shows a schematic side view of a uterine manipulator device in accordance with the invention;

FIG. 2 shows a schematic top view of the uterine manipulator device of FIG. 1;

FIG. 3 shows a schematic rear end view of the uterine manipulator device of FIG. 1;

FIG. 8 shows an enlarged schematic sectional side view of the nose portion of the uterine manipulator device of FIG. 1, having a bladder mounted thereon, the bladder being uninflated; and FIG. 9 shows an enlarge schematic sectional side view of the nose portion of the uterine manipulator device of FIG. 1, having a bladder mounted thereon, the bladder being inflated.

DESCRIPTION OF THE PREFERRED EMBODIMENT

Figure 4:
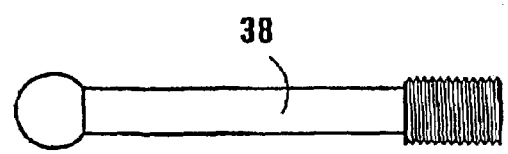
FIG. 4 shows a schematic side view of the extension element of the uterine manipulator device of FIG. 1.
Figure 5:
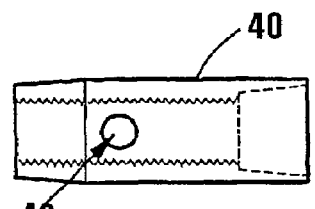
FIG. 5 shows a schematic side view of the connector of the uterine manipulator device of FIG. 1.
Figure 6:
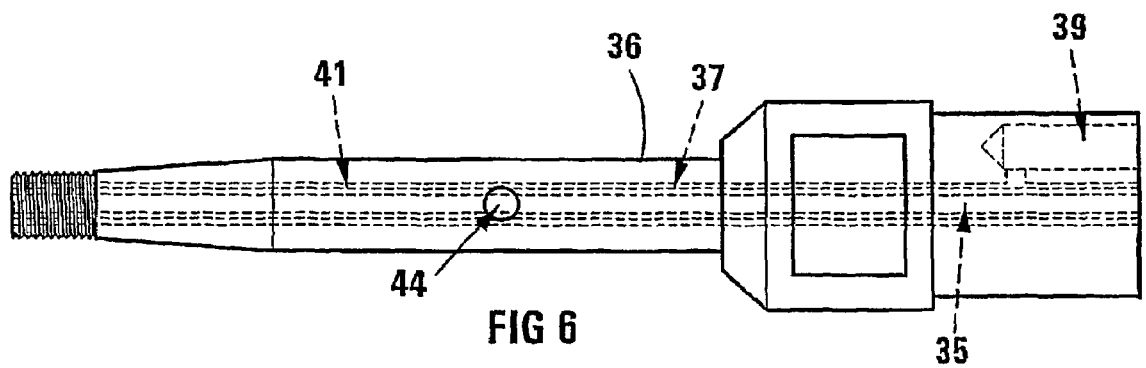
FIG. 6 shows a shows a schematic side view of the nose element of the uterine manipulator device of FIG. 1.
Figure 7:
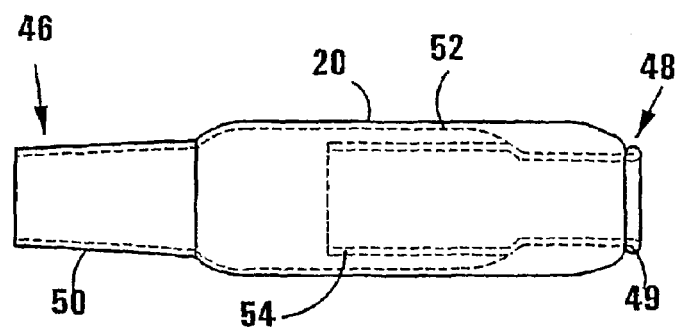
FIG. 7 shows a schematic side view of the bladder of the uterine manipulator device of FIG. 1, showing hidden detail.

With reference to the drawings, a uterine manipulator device, in accordance with the invention, is designated generally by the reference numeral 10. The uterine manipulator device 10 is specifically adapted for performing a laparoscopy wherein the device is used to inject a visualisation fluid into the uterine cavity of a female via the cervix and to manipulate the uterus for enhancing visualisation of the structures of the uterus.

The uterine manipulator device 10 comprises, broadly, an elongate body 12 having a main body portion 14 and a nose portion 16 that is inserted into the cervix, in use, gripping means in the form of a tanaculum 18, for releasably gripping the cervix and sealing means in the form of a disposable bladder 20 for forming a fluid-resistant seal between the nose portion 16 and the cervix.

The elongate body 12 and the gripping arm 18 are of grade 316 stainless steel, whereas the bladder is of resiliently deformable polyurethane plastics material. The elongate body 12 has a front end 17 and rear end 19.

The tanaculum 18 comprises an arm 22 having a hook-like member 24 at one end that hooks, in use, onto the outer cervical lip of the wall of the cervix, and a handle 26 at the other end, for manipulating the hook-like member 24. The handle 26 defines an aperture 28 in which a finger of a person using the device can be received for manipulating the hook-like member 24 in scissors-fashion. The arm 22 is pivotally connected via a pivot pin 30 of a pivot mounting 32, to the main body 14. The main body portion 14 includes a catch formation 34 near the rear end thereof for releasably holding the arm 22 in a closed position wherein the hook-like member 24 hooks into the cervical lip of the wall of the cervix, in use.

The elongate body 12 has a first conduit 35 along which a visualisation fluid can be conveyed into the uterus of a female, in use. The flow direction of the visualisation fluid along the first conduit is shown by the arrows in FIGS. 8 and 9 of the drawings. The elongate body 12 has a second conduit 37 which can be connected to a pressurised air supply and along which pressurised air can flow for inflating the bladder as will be explained in further detail below.

The nose portion 16 of the elongate body includes a nose element 36, an extension element 38 and a connector 40 for connecting the nose element and the extension element. The nose element is connected to the main body portion 14 of the elongate body. The connector defines an internal screw thread formation and the nose element and the extension element define complementary external screw thread formations at connecting ends thereof thereby permitting the nose element and the extension element to be screwed into the connector 40. The screw thread formations are designed so as to provide a fluid-tight seal between the connector and the nose element and the extension element, respectively.

The connector 40 defines an outlet opening 42 which is in flow communication with the first conduit 35 and through which visualisation fluid can flow into the uterus of a female, in use.

The nose element 36 defines an outlet opening 44 which is in flow communication with the second conduit 37 and through which pressurised air can flow into the bladder 20 for inflating it. The second conduit 37 comprises a tubular passage 39 which extends along the length of the main body portion and thereafter becomes an annular passage 41 in the nose element 36, the annular passage surrounding the first conduit 35 and which opens into the outlet opening 44.

The bladder 20 is mounted to the nose element 36 over the outlet opening 44. The bladder 20 has two ends 46 and 48 which each define an opening in which the nose element is received. The ends of the bladder are secured to the nose element 36 so as to form a fluid-tight seal therewith, More particularly, the end 48 defines an O-ring seal 49 which is secured around the nose element. The end 46 defines a tapered tubular section 50 which is clamped between the connector 40 and the nose element as is illustrated in FIGS. 8 and 9. As such, the connector 40 and the nose element define complementary tapered formations defining a gap between them in which the tubular section 50 of the bladder is received and clamped.

The bladder 20 includes an outer inflatable sealing element 52 which, when inflated, conforms to the shape of the cervix forming a fluid-resistant seal therewith. Further, the bladder 20 includes an inner valve element 54 in the form of a sleeve which extends inwardly from a position near the end 48, terminating short of the other end of the bladder. The valve element fits over the outlet opening 44 so as to form a gas-tight seal with the nose element which prevents a return flow of air into the second conduit 37. The valve element is sufficiently deformable to permit it to be deformed under the force of pressurised air in the second conduit so as to allow the flow of air into the bladder for inflating it.

The invention extends to the bladder 20.

In use, in order to perform a laparoscopy on a female, the nose portion of the elongate body, having the bladder 20 mounted thereon, is inserted into the female cervix with the extension element and the nose element extending into the uterine cavity. In order to hold the elongate body in this position, the tenaculum 18 is manipulated so that the hook-like member 24 penetrates the outer cervical lip of the cervix. The handle 26 is then disposed into a closed condition and releasably held in position by the catch 34. In order to form a fluid-tight seal between the wall of the cervix and the nose portion of the elongate body, the second conduit is connected to an air hose and, the bladder is inflated. After an adequate seal is formed between the nose portion and the wall of the cervix, a visualisation fluid is introduced into the first conduit where it is discharged into the uterine cavity via the outlet opening 42. The bladder can be inflated to form a fluid-tight seal along the whole length of the cervical canal. Being deformable, the bladder can be inflated to a required pressure so as to form a fluid-tight seal with cervixes of different sizes and lengths. Another advantage is that the bladder 20 cannot be displaced with uterine movement when the uterus is manipulated, in use.

In another embodiment, the uterine manipulator device may have a configuration rendering it suitable for performing a hystosalpingograms wherein a radio opaque fluid is conveyed along the first conduit of the elongate body into the uterine cavity of a female. In this embodiment, the uterine manipulator device will be the same as that used for preforming laparoscopies, with the only difference being that the nose portion of the elongate body is shorter than that of the uterine manipulator device 10.

The invention claimed is:

1. A uterine manipulator device for injecting a visualisation fluid into the uterus of a female via the cervix, the uterine manipulator device comprising an elongate body that can be inserted into the uterus of the female via the cervix, the elongate body having a visualisation fluid conduit along which the visualisation fluid can be conveyed to the uterus and a gas conduit along which a gas can be conveyed, the gas conduit defining an outlet opening for the gas;

gripping device that is connected to the elongate body, for releasably gripping the cervix; and sealing device that is locatable, in use, in the cervical canal of the female and that is in the form of an inflatable bladder of resiliently deformable material having two ends and defining an opening at each end, the bladder being mounted to the elongate body in an arrangement wherein the bladder surrounds a part of the elongate body, with the elongate body extending through the openings of the bladder and the ends thereof being secured to the elongate body to form a fluid-tight seal therewith, the bladder comprising an outer inflatable sealing element and an inner valve element in the form of a sleeve which extends inwardly from one of the ends of the bladder, terminating short of the other end thereof, the sleeve fitting over the outlet opening of the gas conduit so as to form a gas-tight seal preventing a return-flow of gas into the gas conduit from the bladder, the sleeve being resiliently deformable under the force of a pressurised gas flowing in the gas conduit, in use, so as to allow the flow of gas into the bladder for inflating it to form a fluid-resistant seal between the elongate body and the wall of the cervical canal, in use, thereby preventing a return-flow of visualisation fluid.

2. The uterine manipulator device as claimed in claim 1, wherein the outer inflatable sealing element is substantially elongate and tubular in the inflated state.

3. The uterine manipulator device as claimed in claim 1 or claim 2, wherein the outer inflatable sealing element has a configuration permitting it to conform substantially to the wall of the cervical canal in the inflated state.

4. The uterine manipulator device as claimed in any one of the preceding claims, wherein the elongate body comprises a main body portion and a nose portion that can be inserted into the cervix, the elongate body defining said gas conduit, with the outlet opening thereof being disposed in a region of the nose portion surrounded by the bladder.

5. The uterine manipulator device as claimed in any one of the preceding claims, wherein the gripping means is in the form of a tanaculum.

6. A sealing device for use with a uterine manipulator device for injecting a visualisation fluid into the uterus of a female via the cervix, wherein the uterine manipulator device includes an elongate body that can be inserted into the uterus of the female via the cervix, the elongate body having a visualisation fluid conduit along which the visualisation fluid can be conveyed to the uterus and a gas conduit along which a gas can be conveyed, the gas conduit defining an outlet opening for the gas, the sealing device being locatable, in use, in the cervical canal of the female and being mountable on the elongate body so as to form a fluid-resistant seal between the elongate body and the wall of the cervical canal thereby to prevent a return flow of visualisation fluid, the sealing device comprising an inflatable bladder of resiliently deformable material having two ends and defining an opening at each end, the bladder being mountable to the elongate body in an arrangement wherein the bladder surrounds a part of the elongate body having said outlet opening for the gas conduit, with the elongate body extending through the openings of the bladder and the ends thereof being secured to the elongate body to form a fluid-tight seal therewith, the bladder comprising an outer inflatable sealing element and an inner valve element in the form of a sleeve which extends inwardly from one of the ends of th bladder, terminating short of the other end thereof, the sleeve fitting over the outlet opening of the gas conduit so as to form a gas-tight seal preventing a return-flow of gas into the gas conduit from the bladder, the sleeve being resiliently deformable under the force of a pressurised gas flowing in the gas conduit, in use, so as to allow the flow of gas into the bladder for inflating it to form said fluid-resistant seal between the elongate body and the wall of the cervical canal, in use.

7. The sealing device as claimed in claim 6, wherein the outer inflatable sealing element is substantially elongate and tubular in the inflated state.

8. The sealing device as claimed in claim 6, wherein the outer inflatable sealing element has a configuration permitting it to conform substantially to the wall of the cervical canal in the inflated state.

* * * * *